(12) United States Patent
Toomajian et al.

(10) Patent No.: US 12,090,240 B2
(45) Date of Patent: Sep. 17, 2024

(54) METHOD AND DEVICE FOR DISINFECTION OF HEALTHCARE PERSONAL PROTECTIVE EQUIPMENT BY DIRECT APPLICATION OF A DRY PLASMA FIELD

(71) Applicants: Martin E. Toomajian, Brighton, MI (US); Kevin D. Hawley, Dexter, MI (US)

(72) Inventors: Martin E. Toomajian, Brighton, MI (US); Kevin D. Hawley, Dexter, MI (US)

(73) Assignee: MagPlasma, Inc., Brighton, MI (US)

( * ) Notice: Subject to any disclaimer, the term of this patent is extended or adjusted under 35 U.S.C. 154(b) by 714 days.

(21) Appl. No.: 17/228,624

(22) Filed: Apr. 12, 2021

(65) Prior Publication Data

US 2021/0322606 A1 Oct. 21, 2021

Related U.S. Application Data

(60) Provisional application No. 63/012,168, filed on Apr. 19, 2020.

(51) Int. Cl.
*A61L 2/14* (2006.01)
*H01J 37/32* (2006.01)

(52) U.S. Cl.
CPC .......... *A61L 2/14* (2013.01); *H01J 37/32082* (2013.01); *H01J 37/32449* (2013.01); *H01J 37/32568* (2013.01); *H01J 37/32715* (2013.01); *H01J 37/32834* (2013.01); *A61L 2202/14* (2013.01)

(58) Field of Classification Search
CPC .... A61L 2/14; A61L 2202/11; A61L 2202/14; A61L 2202/26; H01J 37/32082; H01J 37/32091; H01J 37/32449; H01J 37/32568; H01J 37/32715; H01J 37/32834
See application file for complete search history.

(56) References Cited

U.S. PATENT DOCUMENTS

| | | | | |
|---|---|---|---|---|
| 6,096,564 A * | 8/2000 | Denes | ....................... | A61L 2/14 438/1 |
| 6,143,124 A * | 11/2000 | Ahn | .................. | H01J 37/32009 118/623 |
| 6,342,187 B1 * | 1/2002 | Jacob | ....................... | A61L 2/12 422/186.05 |
| 11,532,465 B2 * | 12/2022 | Diener | .................. | C03B 11/127 |
| 2004/0262146 A1 * | 12/2004 | Platt, Jr. | .................... | A61L 2/24 422/23 |

(Continued)

*Primary Examiner* — Jennifer Wecker
*Assistant Examiner* — Brady C Pilsbury
(74) *Attorney, Agent, or Firm* — John A. Miller; Shumaker, Loop & Kendrick, LLP

(57) ABSTRACT

An apparatus for reducing pathogen loading is disclosed. A plasma processing chamber is sealed at one end and a pressure sealable door at the other end, with electrodes within the chamber. A first electrode is coupled to a RF power source and a second electrode is coupled to ground. An inlet port introduces a process gas into the chamber. A vacuum pump draws the process gas into the chamber and exhausts through the pump. An object is positioned within an inside wall of the chamber. A surface of the object is disinfected when a plasma field is generated when RF energy from the electrodes is applied to the introduced process gas.

14 Claims, 4 Drawing Sheets

(56) References Cited

U.S. PATENT DOCUMENTS

| | | | |
|---|---|---|---|
| 2005/0205206 A1* | 9/2005 | Lembersky | A61L 2/0011 |
| | | | 257/E21.252 |
| 2006/0280646 A1* | 12/2006 | Shiosawa | A61L 2/208 |
| | | | 422/23 |
| 2014/0003998 A1* | 1/2014 | Franklin | A61L 2/14 |
| | | | 422/186.29 |
| 2016/0207642 A1* | 7/2016 | Longmier | F03H 1/0037 |

* cited by examiner

METHOD AND DEVICE FOR DISINFECTION OF HEALTHCARE PERSONAL PROTECTIVE EQUIPMENT BY DIRECT APPLICATION OF A DRY PLASMA FIELD

CROSS-REFERENCE TO RELATED APPLICATIONS

This application claims priority to U.S. Provisional Application Ser. No. 63/012,168, filed Apr. 19, 2020, titled "METHOD AND DEVICE FOR DISINFECTION OF HEALTHCARE PERSONAL PROTECTIVE EQUIPMENT BY DIRECT APPLICATION OF A DRY PLASMA FIELD", hereby incorporated by reference in its entirety for all of its teachings.

TECHNICAL FIELD

This invention relates to a plasma disinfection apparatus. More specifically, this invention relates to a plasma disinfection apparatus for deactivating or reducing viral loading on the surface of personal protective equipment (PPE) and corrosion sensitive instruments by way of a dry plasma-based technology.

BACKGROUND OF THE INVENTION

The current COVID-19 pandemic has severely taxed our ability to provide a continuous supply of new personal protective equipment (PPE) for healthcare workers. This has led to the need to provide point-of-use decontamination/disinfection. Conventional hospital disinfection processes, such as steam autoclaving are not viable for use with many of the materials used in disposable PPE and use of corrosive aerosols in conventional plasma disinfection devices degrade materials used in medical appliances. Wet plasma systems use chemical additives to either act as the disinfectant (e.g. hydrogen peroxide) or to be converted into a mixture of reactive species, such as steam being converted to mixed oxidants and oxygen radicals, which then act as the disinfectant. In these processes and devices, plasma fields are not used directly to disinfect but assist other disinfection methods. In the case of hydrogen peroxide-plasma methods, the plasma field is primarily used to convert excess hydrogen peroxide into to water and oxygen prior to venting from the system. Thus, the plasma acts as a filter for the system instead of acting as a disinfectant.

SUMMARY OF THE INVENTION

The device, apparatus, and method of plasma disinfection will rapidly disinfect PPE and corrosion sensitive instruments and can be operated by minimally trained healthcare workers. Unlike wet plasma systems, embodiments of the present invention use dry plasmas, such as non-thermal and radio frequency (RF) induced plasmas, to directly disinfect and restore PPE and other sensitive materials, to a safe and reusable condition so they can be quickly returned to service. In some embodiments, only air is allowed into the plasma processing chamber instead of having to add a gas.

In accordance with one embodiment of the present invention, an apparatus for reducing pathogen loading is disclosed. The apparatus includes a plasma processing chamber sealed at one end and with a pressure sealable door at the other end. Electrodes are coupled within the chamber. A first electrode is coupled to a RF power source and a second electrode is coupled to ground. The apparatus also includes an inlet port for introducing a process gas into the chamber and a vacuum pump for drawing the process gas into the chamber and exhausting through the vacuum pump. The inlet port is coupled to the chamber. The apparatus further includes an object positioned within an inside wall of the chamber. A surface of the object is disinfected when a plasma field is generated when RF energy from the electrodes is applied to the process gas. The object may be, but is not limited to, personal protective equipment (PPE), corrosion sensitive instruments, heat and pressure sensitive materials, or electronics. One or more of these objects may be placed or positioned within the chamber for disinfection.

In some embodiments, at least one fixture is coupled to an inner wall of the chamber and is configured to receive and secure the object. The fixture may be, but is not limited to, a shelf to hold the object or a rack to hang the object. In one embodiment, the fixture may be removably attached to the bottom and top of the inner wall of the chamber. In another embodiment, the fixture may be horizontally mounted to, and extend between, the inner wall of the chamber.

In some embodiments, the apparatus may include a flow controller for controlling a flow rate of the process gas into the chamber according to a set flow rate as an electronic signal. The apparatus may also include a temperature gauge for measuring temperature of the chamber, and a pressure gauge for measuring pressure of the chamber. The apparatus may further include a programmable controller for interfacing with and controlling the vacuum pump, the flow controller, the temperature gauge, and the pressure gauge.

In one embodiment, the first electrode may be positioned along a center axis of the chamber, with the second electrode being the inner wall of the chamber to act as the ground electrode. In an alternative embodiment, the electrodes are positioned longitudinally opposite each other and axially adjacent to the inner chamber wall, separated by sufficient distance or insulative material as to prevent arcing.

The process gas may be, but is not limited to air, argon, oxygen, hydrogen, hydrocarbon, or mixtures thereof.

The pathogens may be, but is not limited to, viruses and bacteria. In one embodiment the virus is a coronavirus. The coronavirus may be, but is not limited to, SARS-CoV-2.

In another embodiment of the present invention, a method of reducing pathogen loading on a surface of an object is disclosed. The method includes supplying a process gas from a gas inlet source into a plasma processing chamber. The method further includes applying RF energy into the chamber to generate a plasma field from the process gas. The method also includes disinfecting the surface of the object. The object is positioned within an inside wall of the chamber, with the plasma field surrounding the object.

In yet another embodiment of the present invention, an apparatus for reducing pathogen loading is disclosed. The apparatus includes a plasma processing chamber sealed at one end and with a pressure sealable door at the other end of the chamber. The chamber includes electrodes coupled within the chamber. A first electrode is coupled to a RF power source and a second electrode is coupled to ground. The apparatus also includes an inlet port, coupled to the chamber, for introducing only air into the chamber, and a vacuum pump for drawing the air into the chamber and exhausting through the vacuum pump. The apparatus further includes a fixture coupled to an inner wall of the chamber. The fixture is configured to receive and secure an object. A surface of the object is disinfected when a plasma field is generated when RF energy from the electrodes is applied to the air. In some embodiments, other process gases, in addition to the air, may be introduced into the chamber. The additional process gases may be, but are not limited to, argon, oxygen, hydrogen, hydrocarbon, or mixtures thereof.

In certain embodiments, the present invention reduces surface contamination and entrained loading of contagions, such as viruses and pathogens, on personal protective equipment (PPE) and sensitive instruments through the use of a portable system that utilizes a vacuum chamber, integrated electrodes, a radio frequency (RF) generator, and gas addition to generate an RF induced plasma field for disinfection of materials. The device, apparatus and method may include measurement and control devices for gas flow (mass or volume), temperature, and pressure and may be controlled by a programmable control module. The present invention may be operated in a variety of atmospheres, and different gases can be added to the system, under vacuum, to enhance the disinfection rate and/or efficiency. The device may be configured as a free-standing floor model that can be moved as needed.

Embodiments of the present invention include the following: a plasma chamber consisting of a cylindrical pressure chamber, sealed at one end with a pressure sealable door at the other end. Mechanical penetrations in the chamber are provided for gas inlet, gas outlet, temperature gauge, pressure gauge, vacuum pump, and other penetrations for wires to service internal RF electrodes, grounding electrodes and thermocouples. Viewports, camera ports, and/or plasma field sensing devices may be added to the chamber to indicate when the plasma field is active. These components may be powered by standard electrical current.

In one embodiment, a plasma generating electrode is located along a center axis of the plasma chamber and a cylindrical inner barrel is located between the center electrode and an inner wall of the plasma pressure chamber to act as a grounding electrode. In other embodiments, plasma generating electrodes may also be placed axially adjacent to the inner chamber walls and separated by sufficient distance or insulative material as to prevent arcing. Fixtures and/or shelves are placed inside the chamber to hold PPE or other equipment for disinfection.

Gases, including air, are introduced at a leading edge of the plasma chamber, are controlled by a volume or mass flow control device, and exhaust through the vacuum pump at the discharge end of the chamber. A plasma field is generated internally within the plasma chamber and may or may not extend the full length of the chamber.

The vacuum pump is capable of creating sufficient negative pressure in the device to initiate and maintain a plasma field in the chamber and withdraw deactivated contagion particles from the chamber. Contagions may be, but are not limited to, COVID-19 or other Corona virus patients.

DETAILED DESCRIPTION OF THE PREFERRED EMBODIMENTS

Figure 1:
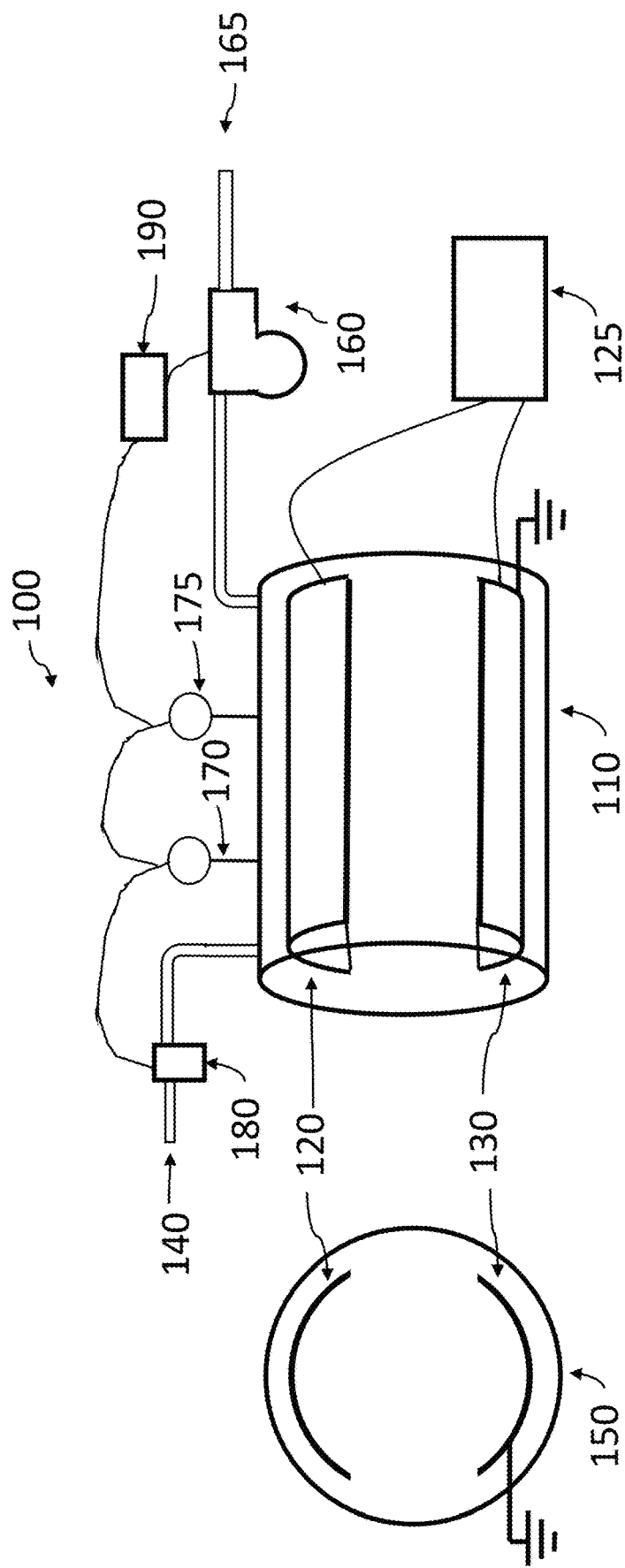
FIG. 1 shows schematic view, along with front view of a chamber, of an apparatus for reducing pathogen loading on a surface of an object, in accordance with one embodiment of the present invention.

FIG. 1 shows schematic view, along with front view 150 of a plasma processing chamber 110, of an apparatus 100 for reducing pathogen loading on a surface of an object, in accordance with one embodiment of the present invention. The apparatus includes the chamber 110, sealed at one end and with a pressure sealable door at the other end. The chamber 110 may be formed of any suitable material such as anodized aluminum, bare aluminum, quartz or ceramic.

The chamber 110 includes an RF electrode 120 and a ground electrode 130. RF electrode 120 is capacitively coupled to an RF generator 125 which includes a RF power source. The plasma generating electrodes 120 and 130 are placed axially adjacent to the inner chamber walls and separated by sufficient distance or insulative material as to prevent arcing. The RF generator 125 is capable of generating RF frequencies between 10 megahertz and 20 megahertz and power outputs between 20 watts to 600 watts of power.

A process gas is introduced into the chamber 110 via an inlet port 140. A mass-flow controller 180, which is used to obtain a controlled supply of the process gas, lets the gas flow in to the chamber 110. Suitable process gases may include air or mixtures of argon, oxygen, hydrogen, hydrocarbon or other gases used as the plasma generating media. Where more than one process gas is supplied to the chamber 110, each process gas may have an independent gas source and mass flow controller.

The flow rate of the gas is provided by the mass flow controller 180 and the pumping rate of a vacuum pump 160 which are adjusted to provide a processing pressure suitable for plasma generation so that subsequent plasma processing may be sustained. Plasma is formed when RF energy from the electrodes 120 and 130 is applied to the introduced process gas.

The vacuum pump 160, which is coupled to an outlet of the chamber 110, draws ambient air or additional reactive gases into the chamber 110 and evacuates through a gas outlet to the vacuum pump 160 and to an exhaust line or port 165. The vacuum pump 160 is capable of creating pressure ranges from 1 millibar to 200 millibar to initiate and maintain a plasma within the chamber 110.

Mechanical penetrations in the chamber 110 are provided for the gas inlet 140, a temperature gauge 170, a pressure gauge 175, the vacuum pump 160, and other penetrations for wires to service internal electrodes and thermocouples. Pressure gauge 175 is operable to sense the vacuum pressure within a processing space of the chamber 110 and provides a pressure feedback signal to a system controller 190. Temperature gauge 170 is used to measure the absolute temperature of the gas in the chamber 110 and provides a temperature feedback signal to the system controller 190. The system controller 190 employs readings of pumping rate, temperature, pressure and mass flow obtained from the respective vacuum pump 160, temperature gauge 170, pressure gauge 175 and mass flow controller 180 to regulate mass flow of the mass flow controller 180.

Figure 2:
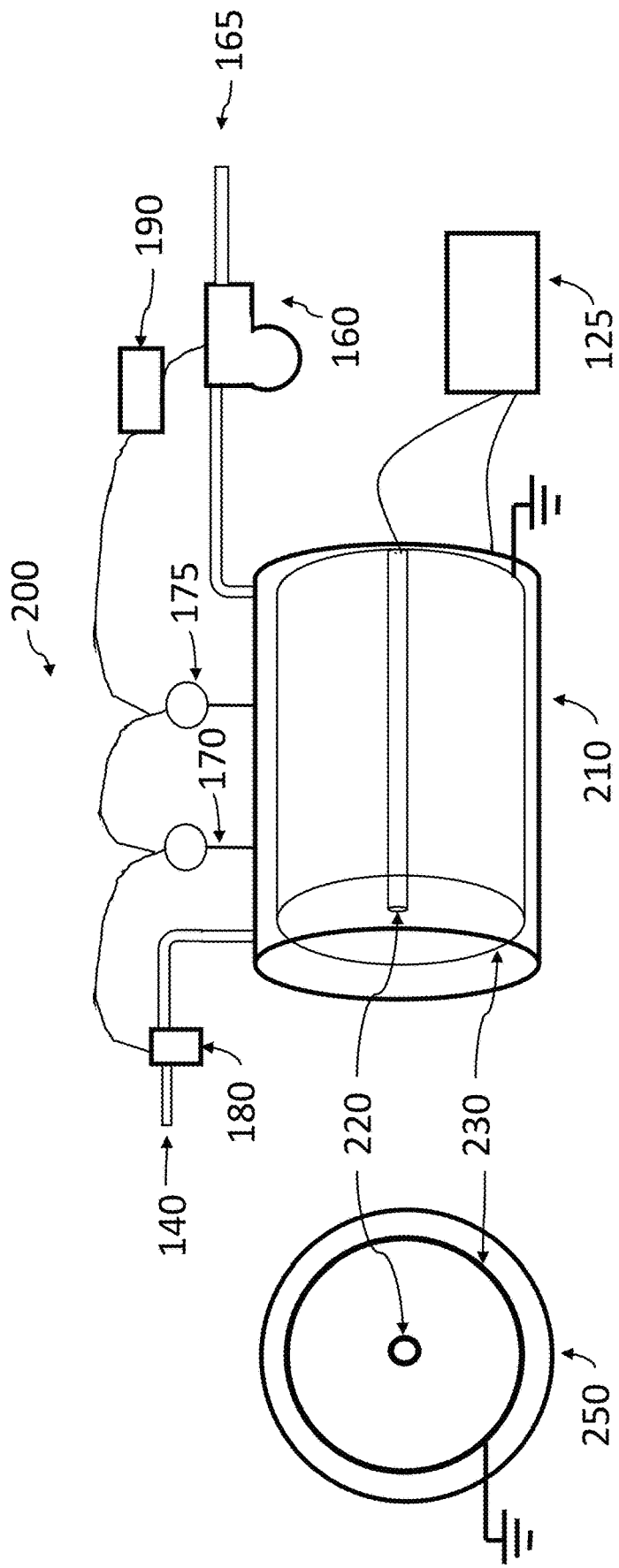
FIG. 2 shows schematic view, along with front view of a chamber, of an apparatus for reducing pathogen loading on a surface of an object, in accordance with one embodiment of the present invention.

FIG. 2 shows schematic view, along with front view 250 of a plasma processing chamber 210, of an apparatus 200 for reducing pathogen loading on a surface of an object, in accordance with one embodiment of the present invention.

The apparatus 200 differs from the apparatus 100 in FIG. 1 by the placement of the plasma generating electrodes 220 and 230 inside the chamber 210. In this embodiment, the electrodes 220 and 230 are concentric, with the RF electrode 220 centered longitudinally in the chamber 210 and the inner wall of the chamber 210 serving as the ground electrode 230. The RF electrode 220 may extend longitudinally more than a majority of the longitudinal distance within the chamber 210, which has the advantage of providing a plasma field along most of the interior of the chamber 210.

Figure 3:
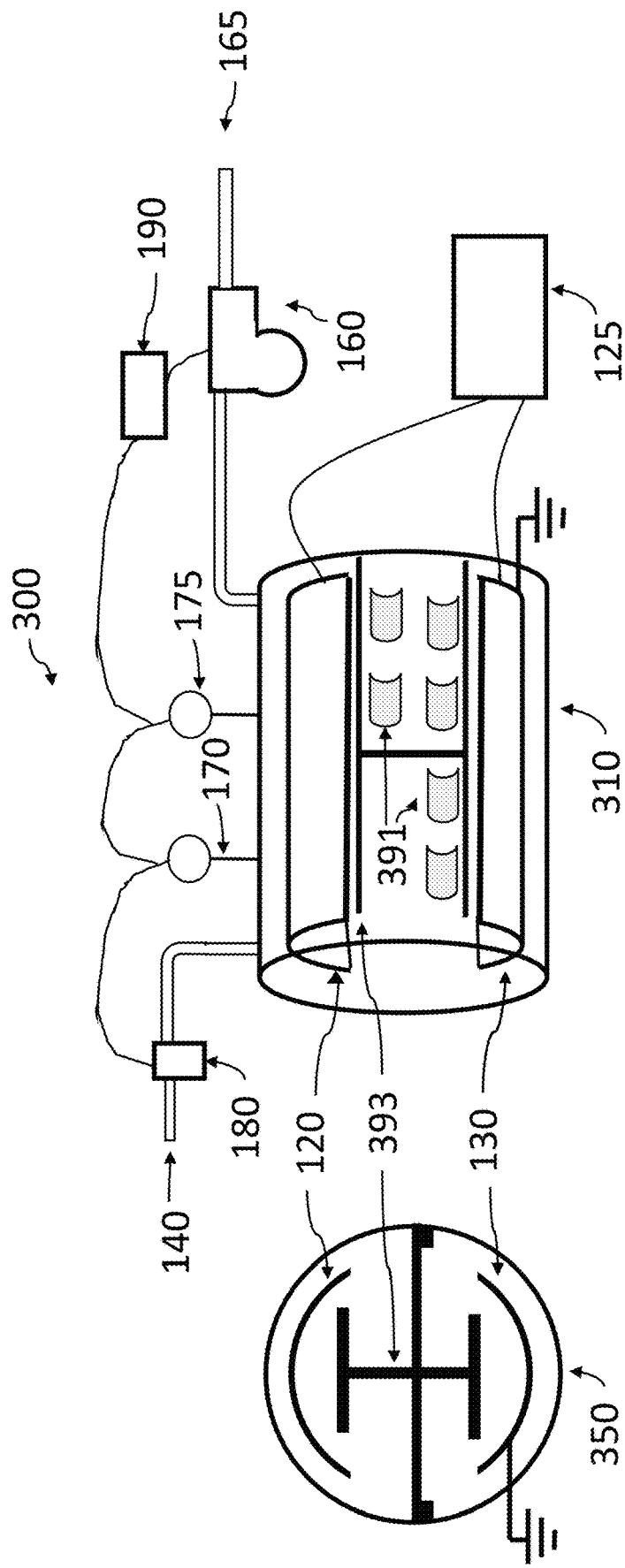
FIG. 3 shows schematic view, along with front view of a chamber, of an apparatus for reducing pathogen loading on a surface of an object, in accordance with one embodiment of the present invention.

FIG. 3 shows schematic view, along with front view 350 of a chamber 310, of an apparatus 300 for reducing pathogen loading on a surface of an object, in accordance with one embodiment of the present invention. FIG. 3 depicts the apparatus from FIG. 1, with electrodes 120 and 130 positioned longitudinally opposite each other and axially adjacent to the inner chamber wall, and includes at least one fixture 393 mounted to and horizontally extending between the inner walls of the chamber 210. The fixture 393, which may be removably attached to the walls, is configured to receive and secure one or more objects 391 to be disinfected by the plasma field in the chamber 310. In one embodiment, the fixture 393 is a shelf for supporting or holding the objects 391. In another embodiment, the fixture 393 is rack to hang the objects 391.

In the embodiment of FIG. 2, with concentric electrodes 220 and 230 and the RF electrode 220 positioned along a center axis of the chamber 210, the internal fixture 393 would be coupled to the floor and top of the inner walls of the chamber 210 to allow for placement of the central RF electrode 220. As with FIG. 3, the fixture 393 may be removably attached to the walls, configured to receive and secure the objects 391 to be disinfected by the plasma field in the chamber 310, and, in some embodiments, may be a shelf for supporting or holding the objects 391 or a rack to hang the objects 391.

Figure 4:
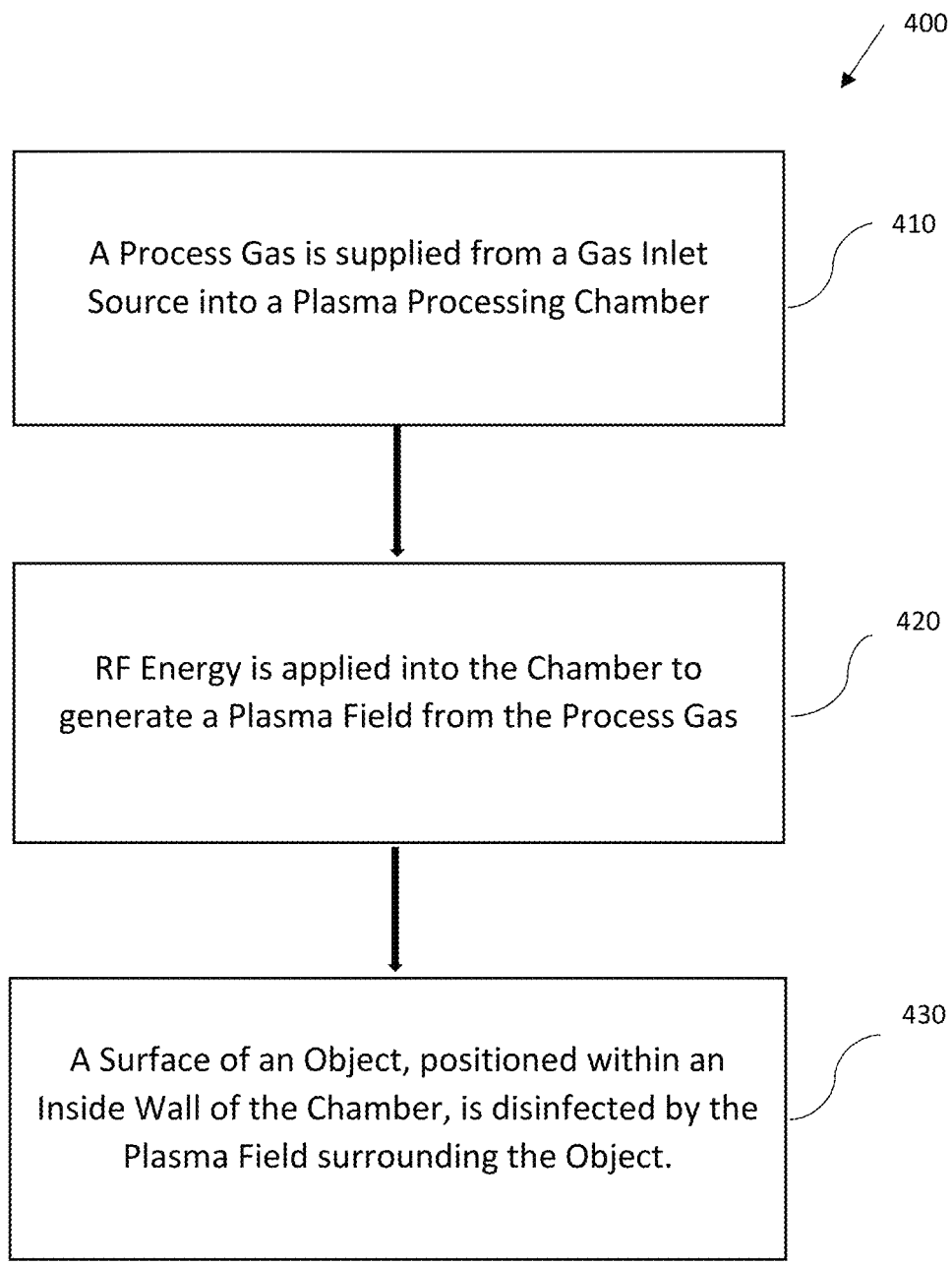
FIG. 4 is a flowchart illustration of a method of reducing pathogen loading on a surface of an object, in accordance with one embodiment of the present invention.

FIG. 4 is a flowchart 400 illustration of a method of reducing pathogen loading on a surface of an object, in accordance with one embodiment of the present invention. In 410, a process gas is supplied from a gas inlet source into a plasma processing chamber. Next, in 420, RF energy is applied into the chamber to generate a plasma field from the process gas. A surface of the object, positioned within an inside wall of the chamber, is disinfected by the plasma field surrounding the object in 430.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

We claim:

1. An apparatus for reducing pathogen loading comprising:
   a. a cylindrical plasma processing outer chamber extending along a longitudinal direction and being sealed at one end and including a pressure sealable door at an opposite end, said processing chamber including a first electrode positioned within the chamber and being coupled to a radio-frequency (RF) power source and a second electrode positioned within the chamber and being coupled to ground, said first electrode being an arced electrode having a same general contour as the cylindrical chamber and extending along the longitudinal direction and said second electrode opposing the first electrode and defining a gap therebetween and being an arced electrode having the same general contour as the cylindrical chamber and extending along the longitudinal direction;
   b. an inlet port, coupled to the chamber, for introducing a process gas into the chamber;
   c. a vacuum pump for drawing the process gas into the chamber; and exhausting through the vacuum pump; and
   d. a fixture for holding an object within the chamber, said fixture including a plurality of support pieces including only a first transverse piece extending between the first and second electrodes and being directly connected to opposing sides of the chamber, a first longitudinal piece extending in the longitudinal direction proximate the first electrode and between the first and second electrodes, a second longitudinal piece extending in the longitudinal direction proximate the second electrode and between the first and second electrodes, and a second transverse piece coupled to the first and second longitudinal pieces and being perpendicular to and extending through the first transverse piece, wherein a surface of the object is disinfected when a plasma field is generated when RF energy from the electrodes is applied to the introduced process gas.

2. The apparatus of claim 1 further comprising: a flow controller for controlling a flow rate of the process gas into the chamber according to a set flow rate sent as an electronic signal, a temperature gauge for measuring temperature of the chamber and a pressure gauge for measuring pressure of the chamber, and a programmable controller for interfacing with and controlling the vacuum pump, the flow controller, the temperature gauge, and the pressure gauge.

3. The apparatus of claim 1 wherein the fixture is removably attached to the chamber.

4. The apparatus of claim 1 wherein the process gas is one of the following: air, argon, oxygen, hydrogen, hydrocarbon, and mixtures thereof.

5. The apparatus of claim 1 wherein the object is at least one of the following: personal protective equipment (PPE), corrosion sensitive instruments, heat and pressure sensitive materials, and electronics.

6. The apparatus of claim 1 wherein the pathogens are viruses.

7. The apparatus of claim 6 wherein the viruses are corona viruses including SARS-COV-2.

8. An apparatus for reducing pathogen loading comprising:
   a. a cylindrical plasma processing outer chamber extending along a longitudinal direction and being sealed at one end and including a pressure sealable door at an opposite end, said processing chamber including electrodes coupled within the chamber, wherein a first electrode is coupled to a radio-frequency (RF) power source and a second electrode is coupled to ground;
   b. an inlet port, coupled to the chamber, for introducing air into the chamber;
   c. a vacuum pump for drawing the air into chamber and exhausting through the vacuum pump; and
   d. a fixture for holding an object within the chamber, said fixture including a plurality of support pieces only including a first transverse piece extending between the first and second electrodes and being directly connected to opposing sides of the chamber, a first longitudinal piece extending in the longitudinal direction proximate the first electrode and between the first and second electrodes, a second longitudinal piece extending in the longitudinal direction proximate the second electrode and between the first and second electrodes, and a second transverse piece coupled to the first and second longitudinal pieces and being perpendicular to and extending through the first transverse piece, wherein a surface of the object is disinfected when a plasma field is generated when RF energy from the electrodes is applied to the introduced air.

9. The apparatus of claim 8 wherein the first electrode is positioned along a center axis of the chamber, and the second electrode being the chamber to act as the ground electrode.

10. The apparatus of claim 8 wherein the electrodes are positioned longitudinally opposite each other and axially adjacent to chamber and separated by sufficient distance or insulative material as to prevent arcing.

11. The apparatus of claim 8 further comprising process gases, in addition to the air, introduced into the chamber, wherein the process gases include at least one of the following: argon, oxygen, hydrogen, hydrocarbon, and mixtures thereof.

12. The apparatus of claim 11 further comprising a flow controller for controlling a flow rate of the process gas into the chamber according to a set flow rate sent as an electronic signal, a temperature gauge for measuring temperature of the chamber and a pressure gauge for measuring pressure of the chamber, and a programmable controller for interfacing with and controlling the vacuum pump, the flow controller, the temperature gauge, and the pressure gauge.

13. The apparatus of claim 8 wherein the object is at least one of the following: personal protective equipment (PPE), corrosion sensitive instruments, heat and pressure sensitive materials, and electronics.

14. The apparatus of claim 8 wherein the fixture is removably attached to the chamber.

* * * * *